United States Patent
Jouvin et al.

(10) Patent No.: US 6,307,186 B1
(45) Date of Patent: Oct. 23, 2001

(54) HYDROCOLLOID PROCESSING MODULE

(76) Inventors: Jean-Luc Jouvin; Frédéric Jouvin, both of 41 Rue de La PerLe, 72000 Le Mans (FR)

( * ) Notice: Subject to any disclaimer, the term of this patent is extended or adjusted under 35 U.S.C. 154(b) by 0 days.

(21) Appl. No.: 09/442,731

(22) Filed: Oct. 22, 1999

(30) Foreign Application Priority Data

Apr. 24, 1997 (FR) .................................................. 97 05090
Apr. 24, 1998 (WO) .................................. PCT/FR98/00832

(51) Int. Cl.[7] ............................. H05B 3/10; A61C 13/20; A61C 13/38
(52) U.S. Cl. .......................... 219/433; 219/521; 219/432; 219/385; 219/530; 219/535; 219/537
(58) Field of Search ..................................... 219/385, 386, 219/430, 432, 433, 436, 521, 530, 535, 537, 539, 540, 546; 237/3, 14; 435/809

(56) References Cited

U.S. PATENT DOCUMENTS

| | | | |
|---|---|---|---|
| 2,932,718 | * 4/1960 | Marsters | 219/430 |
| 3,109,048 | * 10/1963 | Walsh | 219/433 |
| 3,141,948 | * 7/1964 | Young | 219/521 |
| 3,345,497 | * 10/1967 | Porteous | 219/433 |
| 3,607,134 | * 9/1971 | McIntyre | 219/432 |
| 3,801,276 | * 4/1974 | Wagner et al. | 219/430 |
| 4,489,235 | 12/1984 | Porteous . | |
| 4,950,608 | * 8/1990 | Kishimoto | 219/439 |
| 5,306,896 | * 4/1994 | Glater et al. | 219/521 |
| 5,399,840 | * 3/1995 | Goeddeke | 219/521 |

FOREIGN PATENT DOCUMENTS 0 365 144   4/1990   (EP) .
0 603 411   6/1994   (EP) .

* cited by examiner

*Primary Examiner*—Joseph Pelham
(74) *Attorney, Agent, or Firm*—Young & Thompson

(57) ABSTRACT

The invention concerns a device for preparing hydrocolloids comprising means heating a container containing a hydrocolloid. The heating means consist of preferably low-power ceramic resistors, insulated on three surfaces transmitting heat only through the top surface in direct contact with a tube square in external cross section and circular in internal cross section of diameter adapted to the diameter of the hydrocolloid cartridges.

13 Claims, 1 Drawing Sheet

HYDROCOLLOID PROCESSING MODULE

This application is a continuation of copending International Application PCT/FR98/00832, which was filed on Apr. 24, 1998, and designated the United States.

BACKGROUND OF THE INVENTION

1. Field of the Invention

The present invention relates to a module for the preparation and processing of hydrocolloids.

2. Description of the Related Art

Hydrocolloids enable the preparation of precision casts, primarily in the field of dentistry. In order to use hydrocolloids, the material must be heated at 100° C. for approximately 10 minutes in order to transform the gel into a sol, and then tempered at 60° C. to maintain its liquid state. It can then be injected into the buccal cavity, around the teeth and preparations, without the risk of burning the patient.

It is generally covered by another irreversible hydrocolloid called an alginate. The ambient temperature of this alginate cools down the hydrocolloid previously injected around the zones that are difficult to reproduce. This hydrocolloid is much more precise than the alginate but much more expensive, for which reasons it is no longer used exclusively in casts with the water-cooled system integrated in special cast carriers.

At present there are two types of devices for processing hydrocolloids:

water-filled tanks thermostated at 100 and 60° C.;

systems designed exclusively for heating cartridges. These systems handle several cartridges at a time. The cartridges are introduced into a metal (aluminum) unit. A heating element set in the unit provides for its heating; the entire unit is controlled by a microprocessor. The thermal inertia of such systems is high and it is not possible to handle each cartridge separately.

SUMMARY OF THE INVENTION

The goal of the invention is resolve these drawbacks by proposing a device that can be conceived of independently or can be integrated with an alginate malaxator.

For this purpose, the invention comprises a device for the preparation of hydrocolloids that has means for heating a receptacle containing a hydrocoloid, characterized in that said heating means are constituted by low-power, preferably ceramic, resistors 9 of FIG. 1 that are insulated on 3 surfaces and only transmit their heat via the top surface in direct contact with a tube 1 of square external section and circular internal section with a diameter that fits the diameter of the hydrocolloid cartridges 5.

Advantageously, the value of the resistors 2 is between 0.5 and 10 kilo-ohms, preferably between 1 and 4.7 K, with a utilization temperature between −55 and +250° C. These values are set for 220 V and need to be adjusted proportionally for other voltages.

According to a preferred mode of implementation, each resistor 2 is in close contact with a safety thermostat 3 that cuts off the power supply to the resistors 2 when the temperature exceeds a predetermined threshold value.

According to an advantageous variant, the tubes 1 that receive the cartridges 5 are made of an alloy with good thermal conductivity such as aluminum or brass.

According to another variant, the rear part of each tube 1 is dosed and the tube 1 has a window 8 in its top part which allows the curved blade of a micro-contactor 4 to penetrate it, such that contact is made upon insertion of a cartridge and 5 automatically cut when it is removed.

Advantageously, the bottom surface of each resistor 2 has a heat-sensitive resistor 9 emitting a heating control signal.

According to a preferred variant, each cartridge 5 is handled separately such that there can be as many different programs as there are tubes.

According to a preferred mode of implementation, the device in accordance with the invention has a control circuit to perform the following functions:

advance setting for each tube 1 of a maximum temperature and a minimum temperature;

display after introduction of the cartridges 5 of the temperature of the tube;

signaling of the temperature change.

The advantages of the device according to the invention pertain to the following points:

Very compact micro-unit with dimensions of only 8×8×6 cm.

Extremely reduced thermal inertia, allowing an extremely rapid climb in temperature (as well as very rapid cooling down).

DETAILED DESCRIPTION

Figure 1:
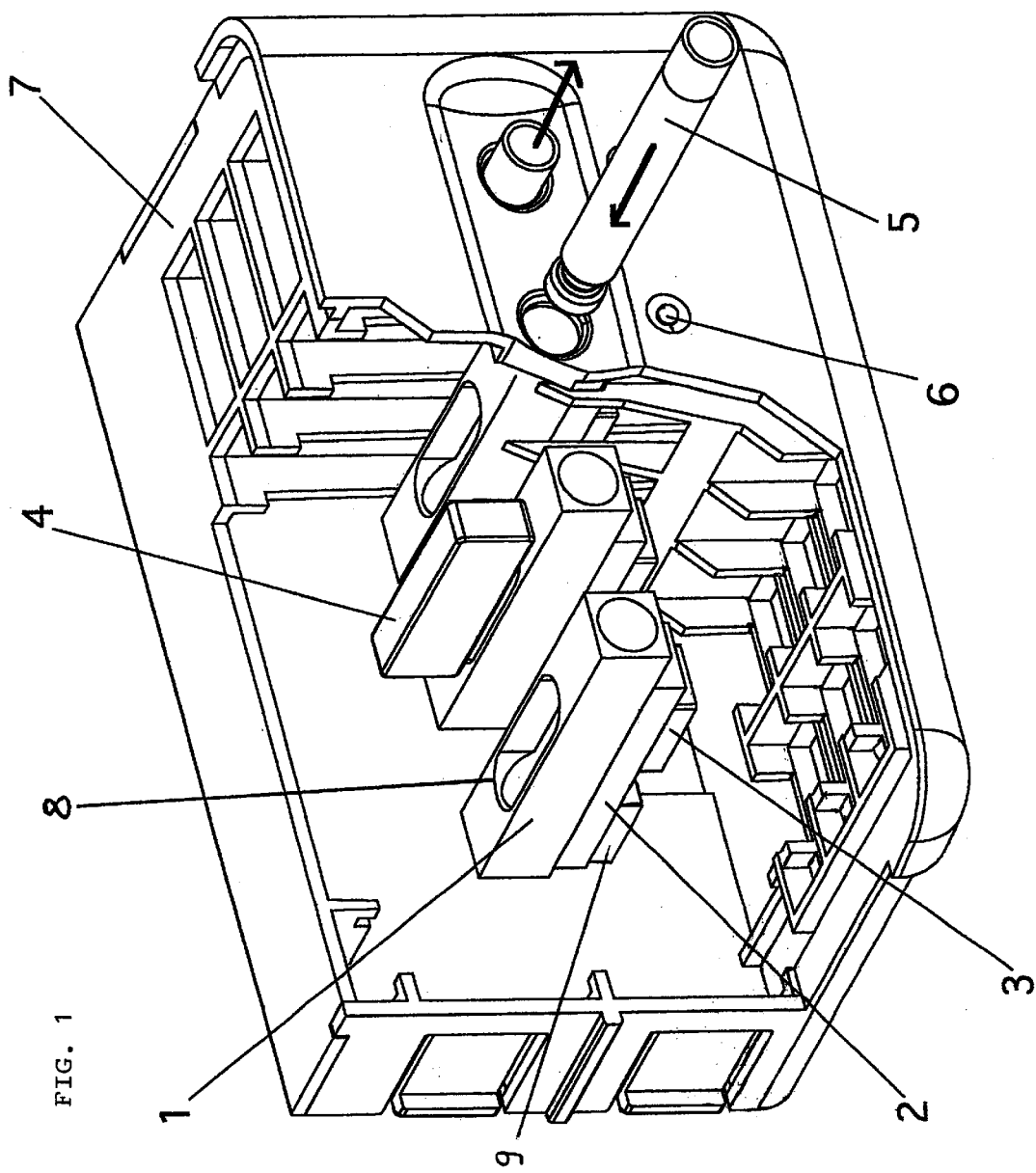
FIG. 1 shows an isometric, partial cut-away view of a hydrocolloid processing module according to one embodiment of the present invention.

In a nonlimitative example of implementation, the device is constituted by a case 7 containing a heating unit formed by bodies, or tubes, of good thermal conduction with their own receptacles to receive the cartridges 5 containing the hydrocolloid to be prepared. Heating is provide by very low-power ceramic resistors 2 with a section of 9×10×50 mm, which are insulated on 3 surfaces and only transmit their heat via the top surface in direct contact with a tube of square external section (10×10 mm). The interior section is circular with a diameter of circa 9 mm so as to fit the diameter of the hydrocolloid cartridges 5. These cartridges 5 are identical to anesthetic cartridges. The value of the resistors 2 is between 0.5K and 10K, preferably between 1 and 4.7K, with a utilization temperature between −55 and +250° C.

Each resistor 9 is in close contact with a safety thermostat 3 that cuts of the power supply to the resistors if the temperature-exceeds 120° C.

These tubes 1 that contain the cartridges 5 weigh only a few grams. They are made of an extremely conductive alloy: aluminum or brass; the latter is better because it can be welded. The rear part of each tube 1 is dosed for safety reasons (explosion of a cartridge). Each tube 1 has a window 8 in its top part to allow penetration of the curved blade of a microcontactor 4 such that contact is made upon insertion of a cartridge 5 and automatically cut when it is removed.

The microcontactors 4 employed are of a special temperature-resistant type.

On the bottom surface of each resistor 2 is glued a "CTN" resistor by means of a temperature-resistant glue (or any other system that allows temperature control). The CTN resistor can also be placed on the rear surface of the brass or aluminum drum. This resistor with a precision of 1% will provide information to the microprocessor regarding the temperature of each ceramic resistor, and thus of each cartridge-carrier tube.

Thus, each cartridge is handled separately such that there can be as many different programs as there are tubes.

The program breaks down as follows:

For each tube 1, it is necessary to set a maximum temperature and a minimum temperature. For hydrocolloids, the maximum temperature is between 95 and 100° C. and the minimum temperature is between 60 and 65° C.; for anesthetics, the two values are set to the same temperature between 30 and 35° C. The program is such that when the maximum temperature is reached, it is maintained for 10 minutes, in accordance with the specifications of the manufacturers of hydrocolloids, and then it redescends to the minimum temperature and that temperature is maintained until removal of the cartridge.

The user inserts the cartridge; the temperature of the tube is then displayed.

To start the heating program, it is necessary to press the button once. While the temperature is climbing, the LED 6 is red and blinking. When the maximum temperature is reached, it remains red but without blinking for 10 minutes. Then it lights up green and blinking during the descent to the minimum temperature. Once that temperature has been reached, the light remains green but not blinking until the cartridge is removed.

If the user wishes to reinsert a still hot partially used cartridge, he pushes the button twice which will cause the unit to maintain the minimum temperature but without repeating the cycle. In practice, the quality of the product deteriorates after 3 heating cycles.

A third push on the button with the cartridge in place stops the system.

Removal of a cartridge irrespective of the cycle stops everything in the tube in question and displays the temperature.

For anesthetics, when the two minimum and maximum temperatures are equal, for example, to 30 or 35° C., the LED 6 blinks green during the temperature climb and then becomes a constant green when the temperature is reached.

The invention has been described above as a nonlimitative example. It is obvious that an expert in the art could implement variants of implementation without, however, going beyond the scope of the invention.

What is claimed is:

1. An apparatus for preparing hydrocolloids comprising:
    (a) thermally conducting bodies each having a receptable configured to receive a cartridge containing a hydrocolloid and each receptable configured with a different heater to heat the hydrocolloid in the corresponding cartridge; and
    (b) a controller configured to independently control each heater of each receptable to independently prepare each hydrocolloid in each cartridge.

2. The apparatus of claim 1, wherein each heater comprises a low-power ceramic resistor insulated on three surfaces and configured to the corresponding receptacle to transmit heat from a fourth uninsulated side of the resistor in direct contact with the corresponding receptacle.

3. The apparatus of claim 1, wherein the controller is configured to independently control the temperature in each receptacle between about 30° C. and about 100° C.

4. The apparatus of claim 1, further comprising a security thermostat that cuts off power to the heaters when the temperature in a receptacle exceeds a predetermined threshold value.

5. The apparatus of claim 1, wherein each receptacle is closed at a rear part of the receptacle and each receptacle has a window in its top part that enables a curved blade of a microcontactor to penetrate it, such that contact is made upon insertion of a cartridge and contact is automatically cut when the cartridge is removed.

6. The apparatus of claim 1, wherein each heater has a heat-sensitive resistor emitting a heating control signal to the controller.

7. The apparatus of claim 1, wherein:
    the controller is configured to be programmed with a different specified minimum temperature and a different specified maximum temperature for each receptacle; and
    the controller is configured with a display that indicates the temperature in each receptacle.

8. The apparatus of claim 7, wherein, for each receptacle, the controller is configured to:
    (1) raise the temperature in the receptacle to the corresponding maximum temperature;
    (2) then maintain the maximum temperature for a predetermined period of time;
    (3) then lower the temperature to the corresponding minimum temperature; and
    (4) then maintain the minimum temperature.

9. The apparatus of claim 8, wherein, when the minimum and maximum temperatures are the same, the controller is configured to achieve and maintain that same temperature.

10. The apparatus of claim 8, wherein the controller comprises an LED display for each receptacle to indicate status of heating operations for that receptacle.

11. The apparatus of claim 1, wherein each receptacle has a circular interior cross-section to receive a cylindrically shaped cartridge.

12. The apparatus of claim 1, wherein the controller is configured to terminate heating operations for a receptacle when the corresponding cartridge is removed.

13. The apparatus of claim 1, wherein:
    further comprising a security thermostat that cuts off power to the heaters when the temperature in a receptacle exceeds a predetermined threshold value;
    each heater comprises a low-power ceramic resistor insulated on three surfaces and configured to the corresponding receptacle to transmit heat from a fourth uninsulated side of the resistor in direct contact with the corresponding receptacle;
    the controller is configured to independently control the temperature in each receptacle between about 30° C. and about 100° C.;
    each receptacle is closed at a rear part of the receptacle and each receptacle has a window in its top part that enables a curved blade of a microcontactor to penetrate it, such that contact is made upon insertion of a cartridge and contact is automatically cut when the cartridge is removed;
    each heater has a heat-sensitive resistor emitting a heating control signal to the controller;
    the controller is configured to be programmed with a different specified minimum temperature and a different specified maximum temperature for each receptacle;
    the controller is configured with a display that indicates the temperature in each receptacle;

for each receptacle, the controller is configured to:
  (1) raise the temperature in the receptacle to the corresponding maximum temperature;
  (2) then maintain the maximum temperature for a predetermined period of time;
  (3) then lower the temperature to the corresponding minimum temperature; and
  (4) then maintain the minimum temperature;
when the minimum and maximum temperatures are the same, the controller is configured to achieve and maintain that same temperature;

the controller comprises an LED display for each receptacle to indicate status of heating operations for that receptacle;

each receptacle has a circular interior cross-section to receive a cylindrically shaped cartridge; and the controller is configured to terminate heating operations for a receptacle when the corresponding cartridge is removed.

* * * * *